(12) United States Patent
Yanke et al.

(10) Patent No.: US 7,473,918 B2
(45) Date of Patent: Jan. 6, 2009

(54) RADIATION-SHIELDING CONTAINER

(75) Inventors: Paul H. Yanke, Mukwonago, WI (US);
Matthew R. Macur, Mukwonago, WI (US); Brian M Schaber, West Allis, WI (US); Thomas J. Ray, Dousman, WI (US)

(73) Assignee: Vulcan Global Manufacturing Solutions, Inc., Milwaukee, WI (US)

( * ) Notice: Subject to any disclaimer, the term of this patent is extended or adjusted under 35 U.S.C. 154(b) by 596 days.

(21) Appl. No.: 11/296,242

(22) Filed: Dec. 7, 2005

(65) Prior Publication Data

US 2007/0129591 A1 Jun. 7, 2007

(51) Int. Cl.
*G21F 5/018* (2006.01)
(52) U.S. Cl. .............. 250/507.1; 250/506.1; 206/365; 600/5
(58) Field of Classification Search .............. 250/507.1, 250/506.1; 206/365; 600/5
See application file for complete search history.

(56) References Cited

U.S. PATENT DOCUMENTS

| | | | |
|---|---|---|---|
| 4,846,235 A * | 7/1989 | Handke | 141/311 R |
| 5,519,931 A | 5/1996 | Reich | |
| 5,536,945 A | 7/1996 | Reich | |
| 5,672,883 A | 9/1997 | Reich | |
| RE36,693 E | 5/2000 | Reich | |
| 6,425,174 B1 | 7/2002 | Reich | |
| 6,722,499 B2 | 4/2004 | Reich | |
| 6,781,142 B2 | 8/2004 | Hutcheson | |
| 6,822,253 B1 | 11/2004 | Martin et al. | |
| 6,963,073 B2 | 11/2005 | Martin et al. | |
| 7,040,856 B2 | 5/2006 | Reich | |
| 2003/0141210 A1 | 7/2003 | Yanke et al. | |
| 2003/0222228 A1 | 12/2003 | Fu et al. | |
| 2004/0016098 A1 | 1/2004 | Reich | |
| 2005/0198800 A1 | 9/2005 | Reich | |
| 2005/0224730 A1 | 10/2005 | Fago et al. | |
| 2005/0234424 A1 | 10/2005 | Besing et al. | |
| 2005/0247893 A1 | 11/2005 | Fu et al. | |

FOREIGN PATENT DOCUMENTS

WO WO 02/17995 3/2002
WO WO 2004/036597 4/2004

* cited by examiner

*Primary Examiner*—Kiet T Nguyen
(74) *Attorney, Agent, or Firm*—Michael Best & Friedrich LLP (57) ABSTRACT

A radiation-shielding container for storing a syringe includes a body assembly and a cap assembly securable to the body assembly such that first and second chamber portions define a chamber for storing the syringe. The body assembly includes a body shield formed of radiation shielding material, a body shell that defines a first cavity having an open end for receiving the body shield and defines a first chamber portion for receiving a portion of the syringe, wherein an inner wall of the body shell separates the first cavity and the first chamber portion, and a body plug secured to the body shell to cover the open end of the first cavity and retain the body shield within the first cavity. The cap assembly includes a cap shield formed of radiation shielding material, a cap shell that defines a second cavity having an open end for receiving the cap shield and defines a second chamber portion for receiving a portion of the syringe, wherein an inner wall of the cap shell separates the second cavity and the second chamber portion, and a cap plug secured to the cap shell to cover the open end of the second cavity and retain the cap shield within the second cavity.

34 Claims, 9 Drawing Sheets

RADIATION-SHIELDING CONTAINER

BACKGROUND

The present invention relates to shielded containers, and more particularly to a radiation-shielding container for storing and transporting a syringe holding a radiopharmaceutical.

Radiation-shielding containers for storing, transporting, and dispensing radioactive drugs are known in the art. Radioactive drugs, commonly known as radiopharmaceuticals, are used to treat a variety of illnesses. However, technicians and medical personnel who handle these drugs on a regular basis must take precautions to reduce their exposure to the radiation emitted by radiopharmaceuticals. These precautions include, among other things, the use of radiation-shielding containers to store radiopharmaceuticals.

Accordingly, radiation-shielding containers that are configured to hold vials of radiopharmaceutical liquid are known. Some containers provide access ports or other openings such that a liquid contained therein can be withdrawn from the vials using a syringe. Other containers exist that are configured to hold an individual syringe that contains radiopharmaceutical liquid. The syringe container is popular among hospitals and other care facilities because the radiopharmaceutical can be shipped and stored in pre-measured doses, thereby reducing the equipment and labor costs associated with storing and handling large quantities of radiopharmaceuticals.

SUMMARY

In one embodiment, the invention provides a radiation-shielding container for storing a syringe. The radiation-shielding container includes a body assembly for housing a portion of the syringe and a cap assembly for housing a portion of the syringe. The body assembly includes a body shield formed of radiation shielding material; a body shell that defines a first cavity having an open end for receiving the body shield and defines a first chamber portion for receiving a portion of the syringe, wherein an inner wall of the body shell separates the first cavity and the first chamber portion; and a body plug secured to the body shell to cover the open end of the first cavity and retain the body shield within the first cavity. The cap assembly includes a cap shield formed of radiation shielding material; a cap shell that defines a second cavity having an open end for receiving the cap shield and defines a second chamber portion for receiving a portion of the syringe, wherein an inner wall of the cap shell separates the second cavity and the second chamber portion; and a cap plug secured to the cap shell to cover the open end of the second cavity and retain the cap shield within the second cavity. The cap assembly is securable to the body assembly such that the first and second chamber portions define a chamber for storing the syringe.

In another embodiment, the invention provides a radiation-shielding container for storing a syringe. The radiation-shielding container includes a body assembly for housing a portion of the syringe and a cap assembly for housing a portion of the syringe, wherein the cap assembly is securable to the body assembly. The body assembly includes a body shell having an outer wall, an inner wall spaced apart from the outer wall, an end wall connecting the outer wall to the inner wall, and an open end. The inner wall defines a first chamber portion for receiving the syringe, and the outer wall, the inner wall and the end wall define a first cavity. A body shield formed of radiation shielding material and having a substantially cylindrical shape is disposed within the first cavity of the body shell wherein an inner surface of the body shield lies adjacent the inner wall of the body shell. A body plug is received by the open end of the body shell to cover the open end and retain the body shield within the first cavity. The cap assembly includes a cap shell having an outer wall, an inner wall spaced apart from the outer wall, an end wall connecting the outer wall to the inner wall, and an open end. The inner wall defines a second chamber portion for receiving the syringe, and the outer wall, the inner wall and the end wall define a second cavity. A cap shield formed of radiation shielding material and having a substantially cylindrical shape is disposed within the second cavity of the cap shell wherein an inner surface of the cap shield lies adjacent the inner wall of the cap shell. A cap plug is received by the open end of the cap shell to cover the open end and retain the shield within the second cavity.

In yet another embodiment, the invention provides a radiation-shielding container for storing a syringe. The radiation-shielding container includes a first assembly for housing a portion of the syringe. The first assembly having a shield formed of radiation shielding material, a shell that defines a first cavity having an open end for receiving the shield and defines a first chamber portion for receiving a portion of the syringe, wherein an inner wall of the shell separates the first cavity and the first chamber portion, and a plug secured to the shell to cover the open end of the first cavity and retain the shield within the first cavity. The radiation-shielding container also includes a second assembly for housing a portion of the syringe. The second assembly includes a shield formed of radiation shielding material and defining a second chamber portion. The first and second assemblies are securable together such that the first and second chamber portions define a chamber for storing the syringe.

The radiation-shielding container includes a first assembly for housing a portion of the syringe and a second assembly for housing a portion of the syringe. The first assembly includes a shield formed of radiation shielding material and having a substantially cylindrical shape, and a protective coating that substantially surrounds and encases the shield. The first assembly defines a first chamber portion. The second assembly includes a shield formed of radiation shielding material and defining a second chamber portion. The first and second assemblies are securable together such that the first and second chamber portions define a chamber for storing the syringe.

In another embodiment the invention provides a method of forming a radiation-shielding container for a syringe. The radiation-shielding container includes a first shell and a second shell, each shell having an outer wall, an inner wall spaced apart from the outer wall, an end wall connecting the outer wall to the inner wall, and an open end, wherein the inner wall defines a chamber portion, and the outer wall, the inner wall and the end wall define a cavity. The method includes placing a first shield in the cavity of the first shell, the first shield formed of radiation shielding material, wherein an inner surface of the first shield is positioned adjacent the inner wall of the first shell. The open end of the first shell is covered to retain the first shield within the cavity of the first shell. A second shield is placed in the cavity of the second shell, the second shield formed of radiation shielding material, wherein an inner surface of the second shield is positioned adjacent the inner wall of the second shell. The open end of the second shell is covered to retain the second shield within the cavity of the second shell. A syringe is placed within the chamber portion of the first shell and the second shell is secured to the first shell wherein the syringe is confined within the chamber portions of the first and second shells.

Other aspects of the invention will become apparent by consideration of the detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

DETAILED DESCRIPTION

Figure 1:
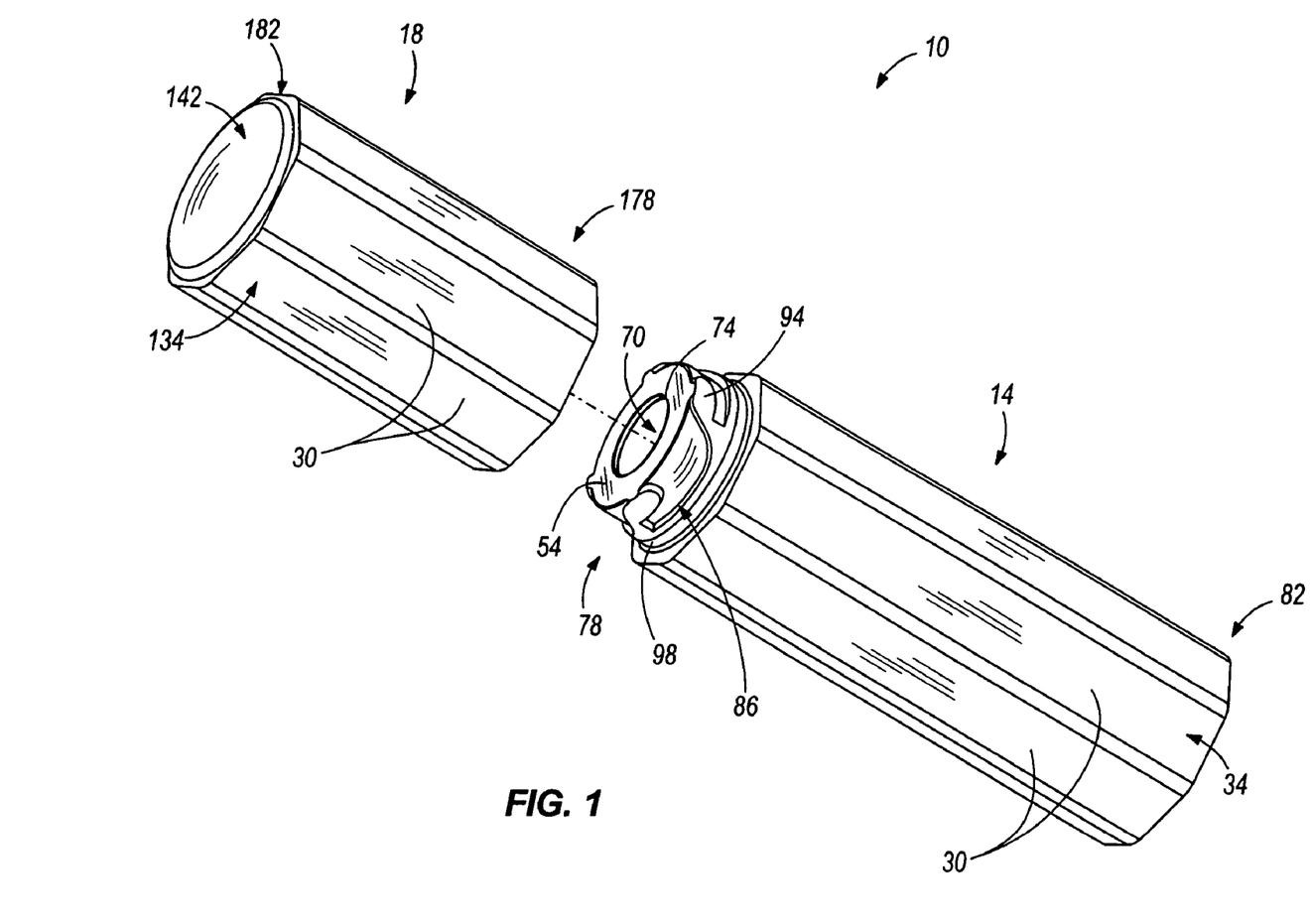
FIG. 1 is a perspective view of a radiation-shielding container, or radiopharmaceutical pig, embodying the invention.
Figure 2:
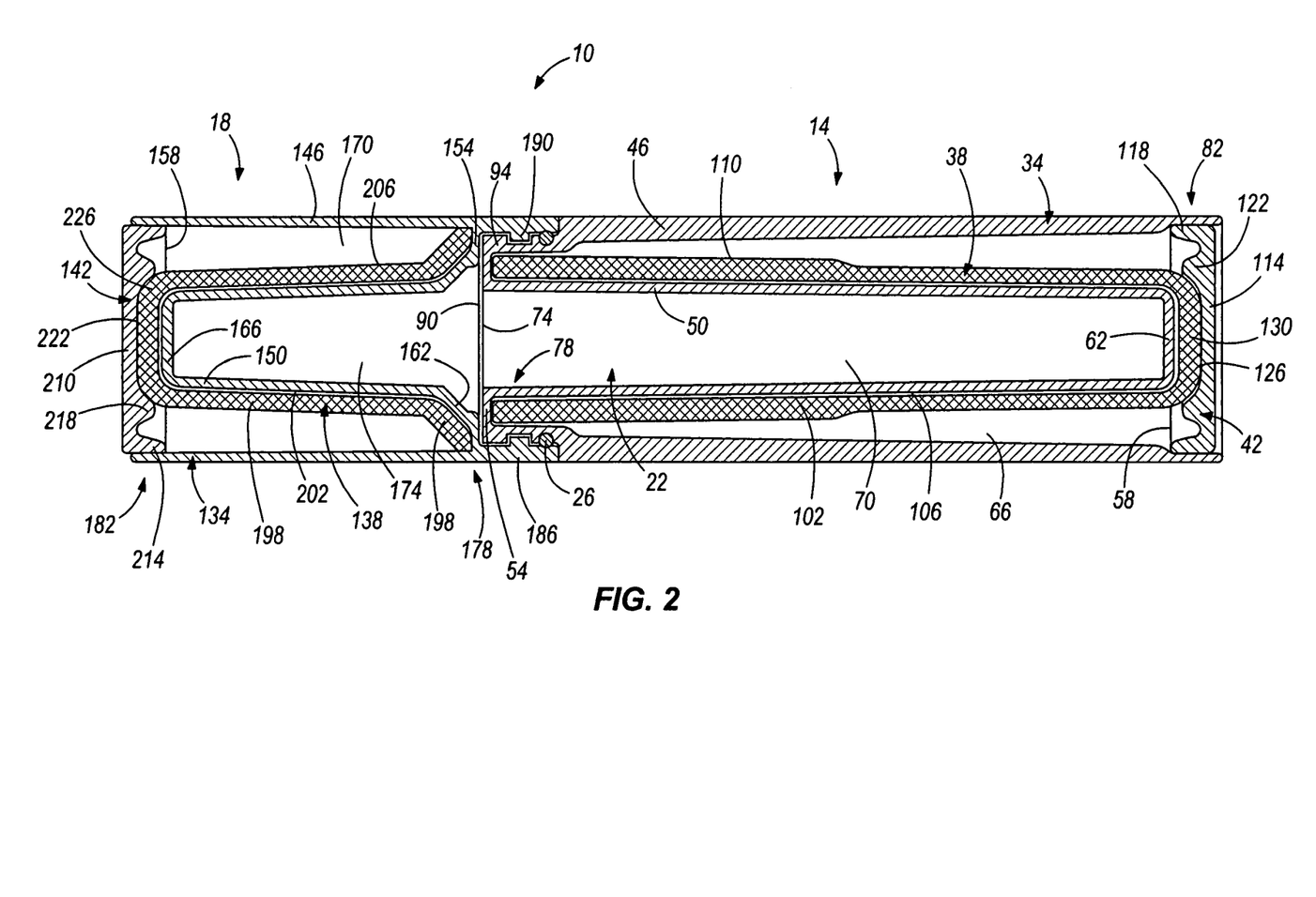
FIG. 2 is a sectional view of the radiation-shielding container with a cap assembly and a body assembly attached.

FIGS. 1 and 2 show a radiation-shielding container 10, often referred to as a radiopharmaceutical pig, for storing and transporting a syringe (not shown) containing a radiopharmaceutical. The container 10 includes radiation shielding to reduce exposure of radiation emitted by the radiopharmaceutical. The container 10 includes a body assembly 14 and a cap assembly 18 removably securable to the body assembly 14. When secured, the body assembly 14 and the cap assembly 18 define a chamber 22 for storing the syringe. The container 10 also includes a resilient O-ring 26 that provides a liquid-tight seal between the body assembly 14 and the cap assembly 18 when the two are secured to one another. In the illustrated embodiment, the body assembly 14 and the cap assembly 18 include a plurality of flats 30, such that each assembly 14, 18 preferably has a substantially octagonal shape, which provide grips to facilitate opening and closing of the container 10.

Figure 3:
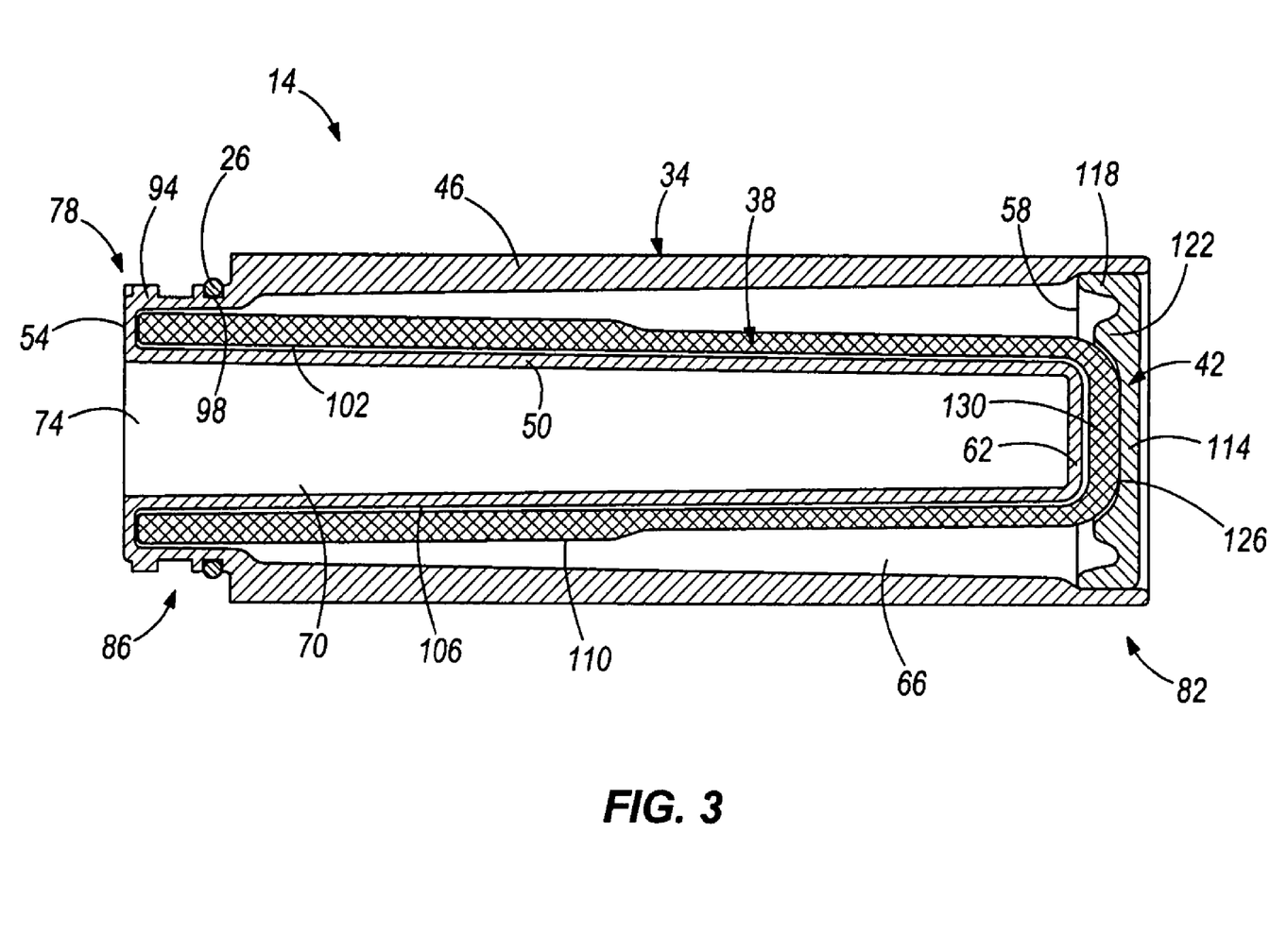
FIG. 3 is a sectional view of the body assembly of the radiation-shielding container.

Referring to FIGS. 1-3, the body assembly 14 includes a shell 34, a shield 38 formed of radiation shielding material that is received within the shell 34, and a plug 42 that retains the shield 38 within the shell 34. The shell 34 is generally cylindrical on the inside and includes an outer wall 46, an inner wall 50 spaced apart from the outer wall 46, a first end wall 54 extending between the outer wall 46 and the inner wall 50, and an open end 58 opposite the end wall 54. A second end wall 62 extends between ends of the inner wall 50 opposite the first end wall 54 and adjacent the open end 58. The outer wall 46, the inner wall 50, and the end walls 54, 62 define a cavity 66 for receiving the shield 38. The inner wall 50 and the second end wall 62 define a first chamber portion 70 for housing a portion of the syringe, wherein the inner wall 50 and the second end wall 62 separate the cavity 66 and the first chamber portion 70. In FIG. 3, an opening 74 of the first chamber portion 70 is located at a first end 78 of the body assembly 14 and the open end 58 of the shell 34 is located at a second end 82 of the body assembly 14.

Proximate the first end 78 of the body assembly 14, a portion of the outer wall 46 of the shell 34 defines a cap-securing structure 86 that extends into an opening 90 of the cap assembly 18. The securing structure 86 defines a plurality of radially outwardly and circumferentially extending ribs 94. In the illustrated embodiment, four ribs are provided and are substantially equally spaced about the circumference of the first end. The cap-securing structure 86 defines a reduced diameter of the shell 34 relative to the remaining portion of the outer wall 46. Axially spaced from the ribs 94 and the first end wall 54 is an annular groove 98 that is adapted to receive the O-ring 26. The O-ring 26 engages the cap assembly 18 to substantially seal the chamber 22 when the cap assembly 18 is secured to the body assembly 14, as set forth hereafter. In the illustrated embodiment, the shell 34 is comprised of a suitable plastic, such as polycarbonate ABS blend, and is formed by injection molding.

The base assembly 14 includes the shield 38 formed of radiation shielding material, such as lead, tungsten or the like. The shield 38 has a generally cylindrical shape and is received within the cavity 66 of the shell 34. An inner surface 102 of the shield 38 lies adjacent the inner wall 50 and the second end wall 62 of the shell 34, however, in the illustrated embodiment there is a clearance fit between the shield 38 and the shell 34. A gap 106 is formed between an outer surface 110 of the shield 38 and the outer wall 46 of the shell 34 such that the shield 38 does not fill the entire cavity 66, which reduces the amount of lead required for the shield 38 and thereby reduces the cost of the container 10. The shield 38 has a thickness sufficient to prevent or reduce exposure of radiation emitted by the radiopharmaceutical. In the illustrated embodiment, the shield 38 has a thickness of about 0.20 inches, however in a further embodiment the thickness is between about 0.10 inches and about 0.25 inches. It should be readily apparent to those of skill in the art that the thickness may fall outside that range as long as the thickness is sufficient to prevent or reduce exposure of radiation emitted by the radiopharmaceutical.

The plug 42 covers the open end 58 of the shell 34 and retains the shield 38 within the shell 34. The plug 42 has a generally circular body portion 114 and includes an outer flange 118 extending axially inward from an outer circumference of the body portion 114, and an inner flange 122 spaced radially inward from the outer flange 118 and extending axially inward from the body portion 114. In use, the plug 42 is inserted into the open end 58 of the shell 34. In the illustrated embodiment, a recess 126 defined by the body portion 114 and the inner flange 122 engages a closed end 130 of the shield 30 and pushes opposite ends of the shield 38 into contact with the first end wall 54 of the shell 34, while maintaining the clearance fit between the inner surface 102 of the shield 38 and the inner wall 50 and the second end wall 54. The plug 42 retains the shield 38 within the cavity 66 and mechanically holds the shield 38 in place within the cavity 66. In the illustrated embodiment, the outer flange 118 is secured to the outer wall 46 of the shell 34, such as by friction welding, bonding, a fastener, or the like. Further, the plug 42 is comprised of a suitable plastic, such as polycarbonate ABS blend, and is formed by injection molding.

Figure 4:
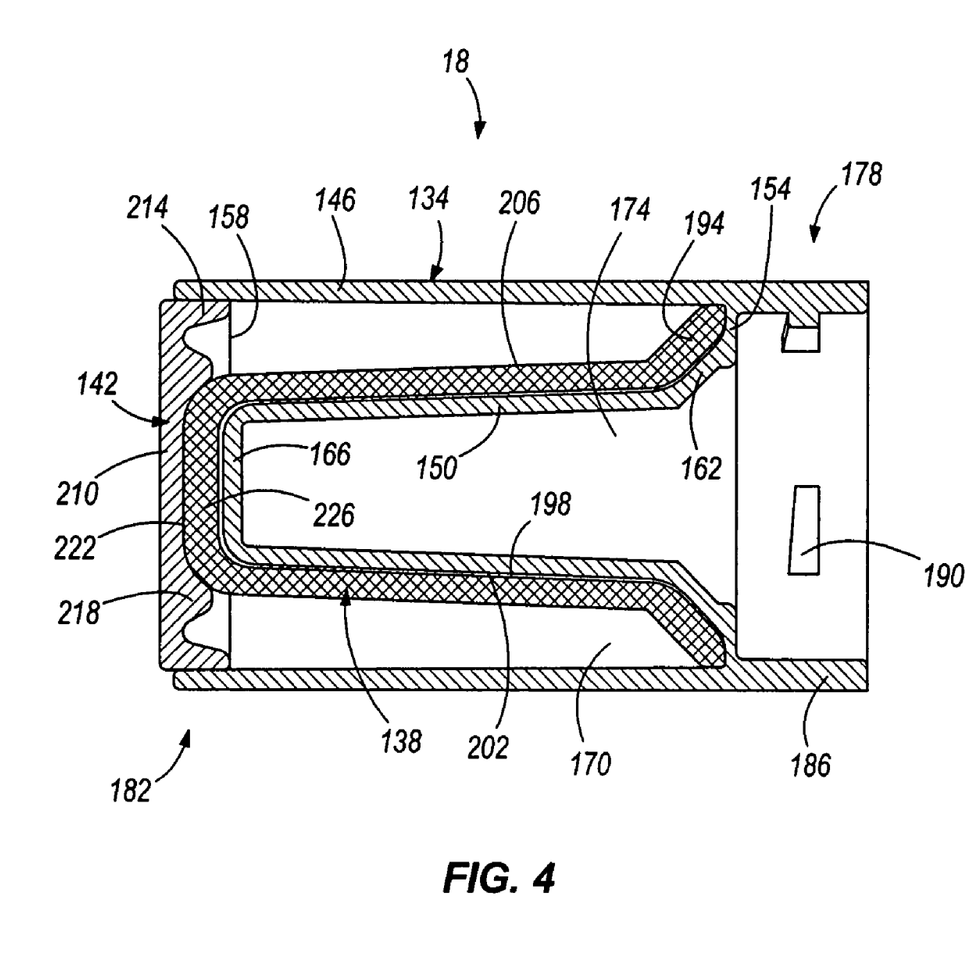
FIG. 4 is a sectional view of the cap assembly of the radiation-shielding container.

Referring to FIGS. 1, 2 and 4, the cap assembly 18 includes a shell 134, a shield 138 formed of radiation shielding material that is received within the shell 134, and a plug 142 that retains the shield 138 within the shell 134. The shell 134 is generally cylindrical on the inside and includes an outer wall 146, an inner wall 150 spaced apart from the outer wall 146, a first end wall 154 extending between the outer wall 146 and the inner wall 150, and an open end 158 opposite the end wall 154. A first end of the inner wall 150 includes an angled portion 162 that extends to the first end wall 154. A second end wall 166 extends between second ends of the inner wall 150 opposite the first end wall 154 and adjacent the open end 158.

The outer wall 146, the inner wall 150, and the end walls 154, 166 define a cavity 170 for receiving the shield 138. The inner wall 150 and the second end wall 166 define a second chamber portion 174 for housing a portion of the syringe, wherein the inner wall 150 and the second end wall 166 separate the cavity 170 and the second chamber portion 174. In FIG. 4, the opening 90 of the second chamber portion 174 is located at a first end 178 of the cap assembly 18 and the open end 158 of the shell 134 is located at a second end 182 of the cap assembly 18. In the illustrated embodiment, the shell is comprised of a suitable plastic, such as polycarbonate ABS blend, and is formed by injection molding.

Proximate the first end 178 of the cap assembly 18, a flange 186 axially extends from the outer wall 146 and the first end wall 154 of the shell 134. The flange 186 defines a body-securing structure in the form of radially inwardly extending projections 190. The projections 190 cooperate with the ribs 94 of the cap-securing structure 86 to provide a releasable attachment between the cap assembly 18 and the body assembly 14. To couple the cap assembly 18 to the body assembly 14, the cap-securing structure 86 is inserted into the opening 90 of the second chamber portion 174 and the cap assembly 18, or the body assembly 14, is rotated approximately one-quarter turn to engage the ribs 94 with the projections 190. In the illustrated embodiment, the body assembly 14 and the cap assembly 18 are secured together by a bayonet-type interlocking means. However, it should be readily apparent to those of skill in the art that in further embodiments other securing structure may be used to secure the body assembly 14 and the cap assembly 18, such as threaded portions, or the securing structure may be reversed between the two assemblies such that the externally projecting ribs on defined by the cap assembly 18 and the internally extending projections are defined by the body assembly 14.

The cap assembly 18 includes the shield 138 formed of radiation shielding material, such as lead, tungsten or the like. The shield 138 has a generally cylindrical shape and is received within the cavity 170 of the shell 134. A first end of the shield 138 defines a flange portion 194 that complements the contour of the inner wall 150 and the angled portion 162 of the shell 134. An inner surface 198 of the shield 138 lies adjacent the inner wall 150 and the second end wall 166 of the shell 134, however, in the illustrated embodiment there is a clearance fit between the shield 138 and the shell 134. A gap 202 is formed between an outer surface 206 of the shield 138 and the outer wall 146 of the shell 134 and the shield 138 does not fill the entire cavity 170, which reduces the amount of lead required for the shield 138 and thereby reduces the cost of the container 10. The shield 138 has a thickness sufficient to prevent or reduce exposure of radiation emitted by the radiopharmaceutical. In the illustrated embodiment, the shield 138 has a thickness of about 0.15 inches, however in a further embodiment the thickness is between about 0.10 inches and about 0.25 inches. It should be readily apparent to those of skill in the art that the thickness may fall outside that range as long as the thickness is sufficient to prevent or reduce exposure of radiation emitted by the radiopharmaceutical.

The plug 142 covers the open end 158 of the shell 134 and retains the shield 138 within the shell 134. In the illustrated embodiment, the plug 142 of the cap assembly 18 is identical to the plug 42 of the body assembly 14 discussed above such that either plug 42, 142 could be used in the body assembly 14 or the cap assembly 18. The plug 142 has a generally circular body portion 210 and includes an outer flange 214 extending axially inward from an outer circumference of the body portion 210, and an inner flange 218 spaced radially inward from the outer flange 214 and extending axially inward from the body portion 210.

In use, the plug 142 is inserted into the open end 158 of the shell 134. In the illustrated embodiment, a recess 222 defined by the body portion 210 and the inner flange 218 engages a closed end 226 of the shield 138 and pushes opposite ends of the shield 138 into contact with the first end wall 154 of the shell 134, while maintaining the clearance fit between the inner surface 198 of the shield 138 and the inner wall 150 and the second end wall 166. The plug 142 retains the shield 138 within the cavity 170 and mechanically holds the shield 138 in place within the cavity 170. In the illustrated embodiment, the outer flange 214 is secured to an inner surface of the outer wall 146 of the shell 134, such as by friction welding, bonding, a fastener, or the like.

To fabricate the radiation-shielding container, the shells 34, 134 for the body and cap assemblies 14, 18, respectively, are formed by injection molding. The radiation shield 38 of the body assembly 14 is placed in the cavity 66 of the body assembly 14 such that the inner surface 102 of the shield 38 is positioned adjacent the inner wall 50 of the shell 34. The plug 42 is secured to the open end 58 of the body assembly shell 34 to cover the open end 58 and mechanically hold the shield 38 in place within the cavity 66. The radiation shield 138 of the cap assembly 18 is placed in the cavity 170 of the cap assembly 18 such that the inner surface 198 of the shield 138 is positioned adjacent the inner wall 150 of the shell 134. The plug 142 is secured to the open end 158 of the cap assembly shell 134 to cover the open end 158 and mechanically hold the shield 138 in place within the cavity 170. In the illustrated embodiment, preferably no adhesive is used to retain or hold the shields 38, 138 within the cavities 66, 170. A syringe (not shown) is placed in the first chamber portion 70 of the body assembly 14. The cap assembly 18 is secured to the body assembly 14 such that the syringe is confined within the chamber 22 defined by the first and second chamber portions 70, 174.

Figure 5:
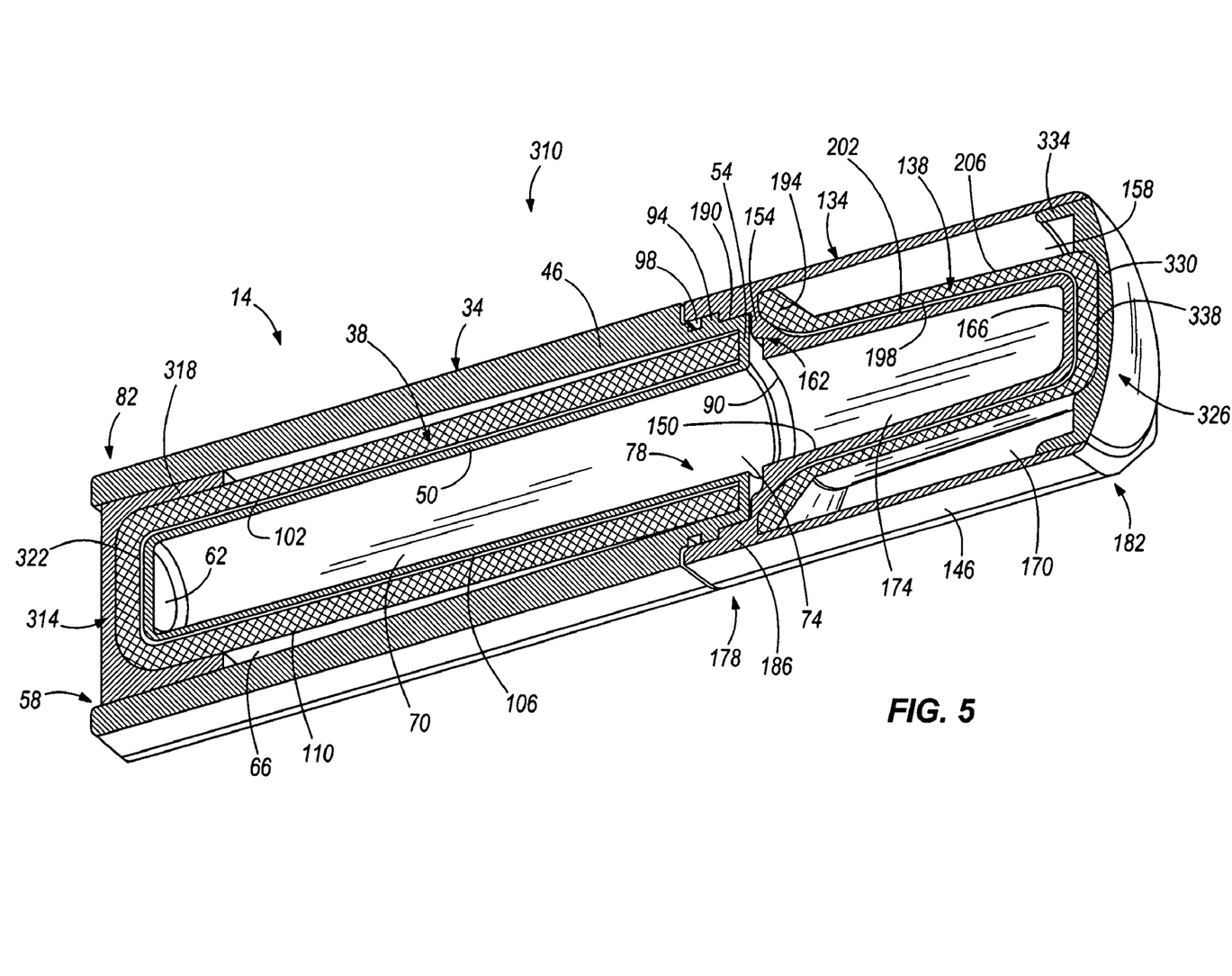
FIG. 5 is a sectional view of another embodiment of a radiation-shielding container.

FIG. 5 illustrates another embodiment of a radiation-shielding container. In FIG. 5, similar features of the radiation-shielding container 10 shown in FIGS. 1-4 are identified by similar reference numerals. A container 310 includes the body assembly 14 and the cap assembly 18 removably securable to the body assembly 14. When secured, the body assembly 14 and the cap assembly 18 define the chamber 22 for storing a syringe (not shown). In a further embodiment, the container 310 includes a resilient O-ring that provides a fluid-tight seal between the body assembly 14 and the cap assembly 18 when the two are secured together.

The body assembly 14 includes the shell 34, the shield 38 formed a radiation shielding matter that is received within the shell 34, and a plug 314 that retains the shield 38 within the shell 34. The shell 34 and the radiation shield 38 are similar to the shell and the radiation shield shown and described above with respect to FIGS. 1-4. The plug 314 covers the open end 58 of the shell 34 and retains the shield 38 within the shell 34. The plug 314 has a generally cylindrical shape and is sized to securely fit within the open end 58 of the shell 34. An outer flange portion 318 of the plug 314 defines an outer circumference that is substantially equal to an inner circumference of the shell 34 at the open end 58. In the illustrated embodiment, a chamber 322 defined by the outer flange portion 328 engages the closed end 130 of the shield 38 and pushes opposite ends of the shield 38 into contact with the first end wall 54 of the shell 34, while maintaining a clearance fit between the inner surface 102 of the shield 38 and the inner wall 50 of the shell 34.

The cap assembly 18 includes the shell 134, the shield 138 formed a radiation shielding matter that is received within the shell 134, and a plug 326 that retains the shield 138 within the shell 134. The shell 134 and the radiation shield 138 of the cap assembly 18 are similar to the shell and the radiation shield shown and described above with respect to FIGS. 1-4. The plug 326 covers the open end 158 of the shell 134 and retains the shield 138 within the shell 134. The plug 326 includes a generally circular body portion 330 and an outer flange 334 extending axially inward from an outer circumference of the body portion 330, such that the plug 326 has a generally cylindrical shape. In use, the plug 326 is inserted into the open end 158 of the shell 134. The outer flange portion 334 of the plug 326 defines an outer circumference that is substantially equal to an inner circumference of the shell 134 at the open end 158. In the illustrated embodiment, a recess 338 defined by the body portion 330 engages the closed end 226 of the shield 138 and pushes opposite ends of the shield 138 into contact with the first end wall 154 of the shell 134, while maintaining a clearance fit between the inner surface 198 of the shield 138 and the inner wall 150 of the shell 134.

The plugs 314, 326 of the body assembly 14 and the cap assembly 18 retain the respective shields 38, 138 within the cavities 66, 170 and mechanically hold the shields 38, 138 in place within the cavities 66, 170. In one embodiment, the outer flange portion 318, 334 of each plug 314, 326 is secured to an inner surface of the outer wall 46, 146 of the respective shell 34, 134, such as by friction welding, bonding, a fastener or the like. Further, the plugs 314, 326 are comprised of a suitable plastic, such as polycarbonate ABS blend, and are formed by injection molding.

Figure 6:
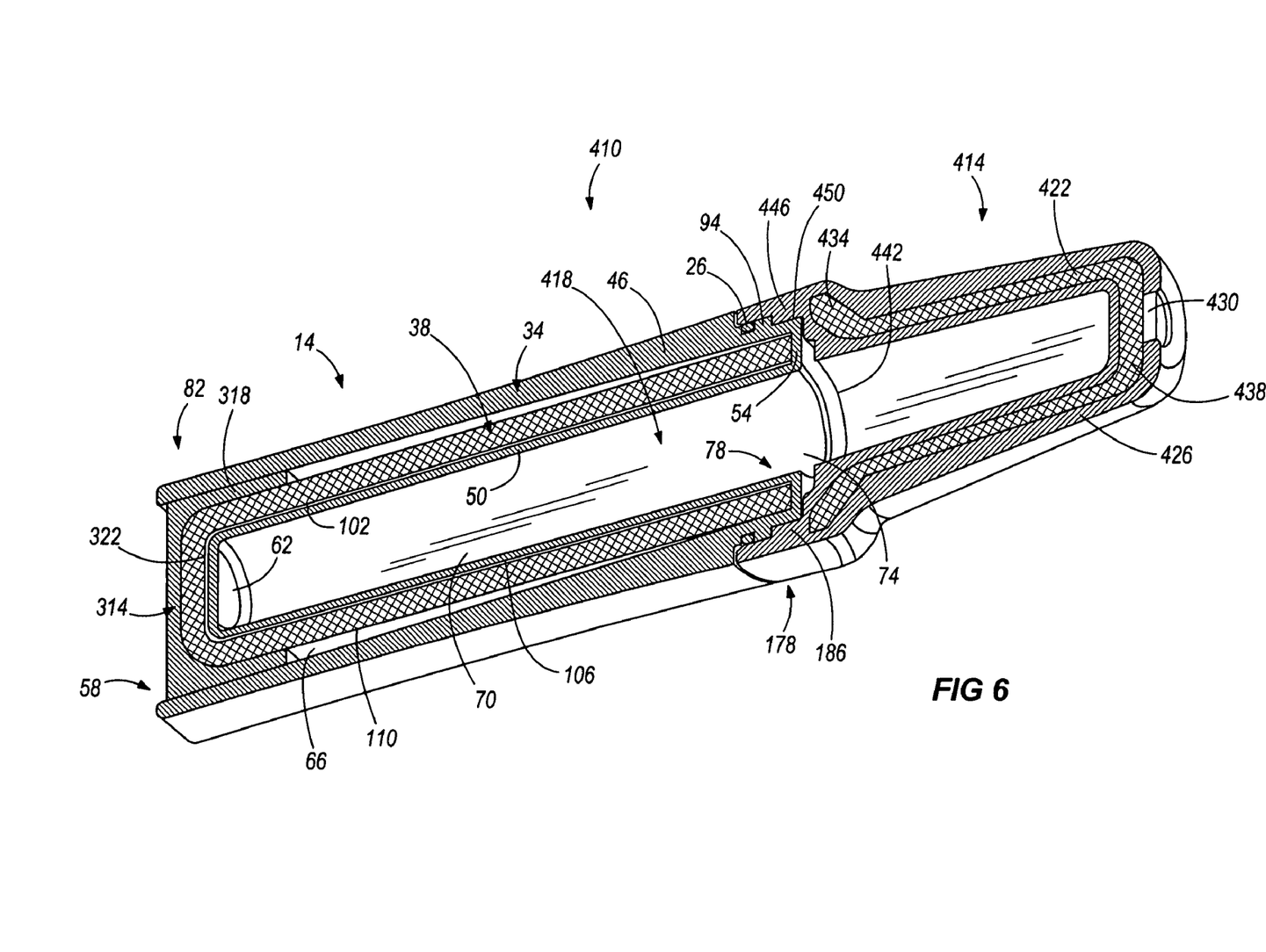
FIG. 6 is a sectional view of another embodiment of a radiation-shielding container.

FIG. 6 illustrates another embodiment of a radiation-shielding container. A container 410 includes the body assembly 14 and a cap assembly 414 removably securable to the body assembly 14. The body assembly 14 is identical to the body assembly shown and described above in FIG. 5, and similar features of the radiation-shielding container 310 shown in FIG. 5 are identified by similar reference numerals. When secured, the body assembly 14 and the cap assembly 414 define a chamber 418 for storing a syringe (not shown). The container 410 also includes the resilient O-ring 26 that provides a fluid-tight seal between the body assembly 14 and the cap assembly 414 when the two are secured together.

The cap assembly 414 includes a shield 422 formed of radiation shielding material (such as lead, tungsten or the like), a protective coating 426, or shell, that surrounds and encases the shield 422, and a plug 430 that covers an exposed portion of the shield 422. The shield 422 has a generally cylindrical shape and a first end of the shield 422 defines a flange portion 434. The shield 422 has a thickness sufficient to prevent or reduce exposure of radiation emitted by the radiopharmaceutical. The shield 422 is overmolded with a homogenous thermoplastic elastomer or thermoset, to form the protective coating 426. The protective coating 426 surrounds and encases the shield 422, except for an open portion located adjacent a second, closed end 438 of the shield 422, to substantially coat all exposed surfaces of the shield 422. The disk-shaped plug 430 is inserted into the open portion of the protective coating 426 to cover the remaining exposed portions of the shield 422. It should be readily apparent to those of skill in the art that other materials and methods may be used for fabricating the shield 422 and the protective coating 426.

Proximate an open end 442 of the cap assembly 414, the protective coating 426 includes a flange 446 that axially extends away from the first end of the shield 422. The flange 446 defines a body-securing structure in the form of radially inwardly extending projections 450. The projections 450 cooperate with the ribs 94 of the cap-securing structure 86 to provide a releasable attachment between the cap assembly 414 and the body assembly 14. To couple the cap assembly 414 to the body assembly 14, the cap-securing structure 86 is inserted into the open end 442 of the cap assembly 414 and the cap assembly 414, or the body assembly 14, is rotated approximately one-quarter turn to engage the ribs 94 with the projections 450. It should be readily apparent to those of skill in the art that in further embodiments other securing structure may be used to secure the body assembly 14 and the cap assembly 414, such as threaded portions, or the securing structure may be reversed between the two assemblies such that the externally projecting ribs are defined by the cap assembly 414 and the internally extending projections are defined by the body assembly 14.

Figure 7:
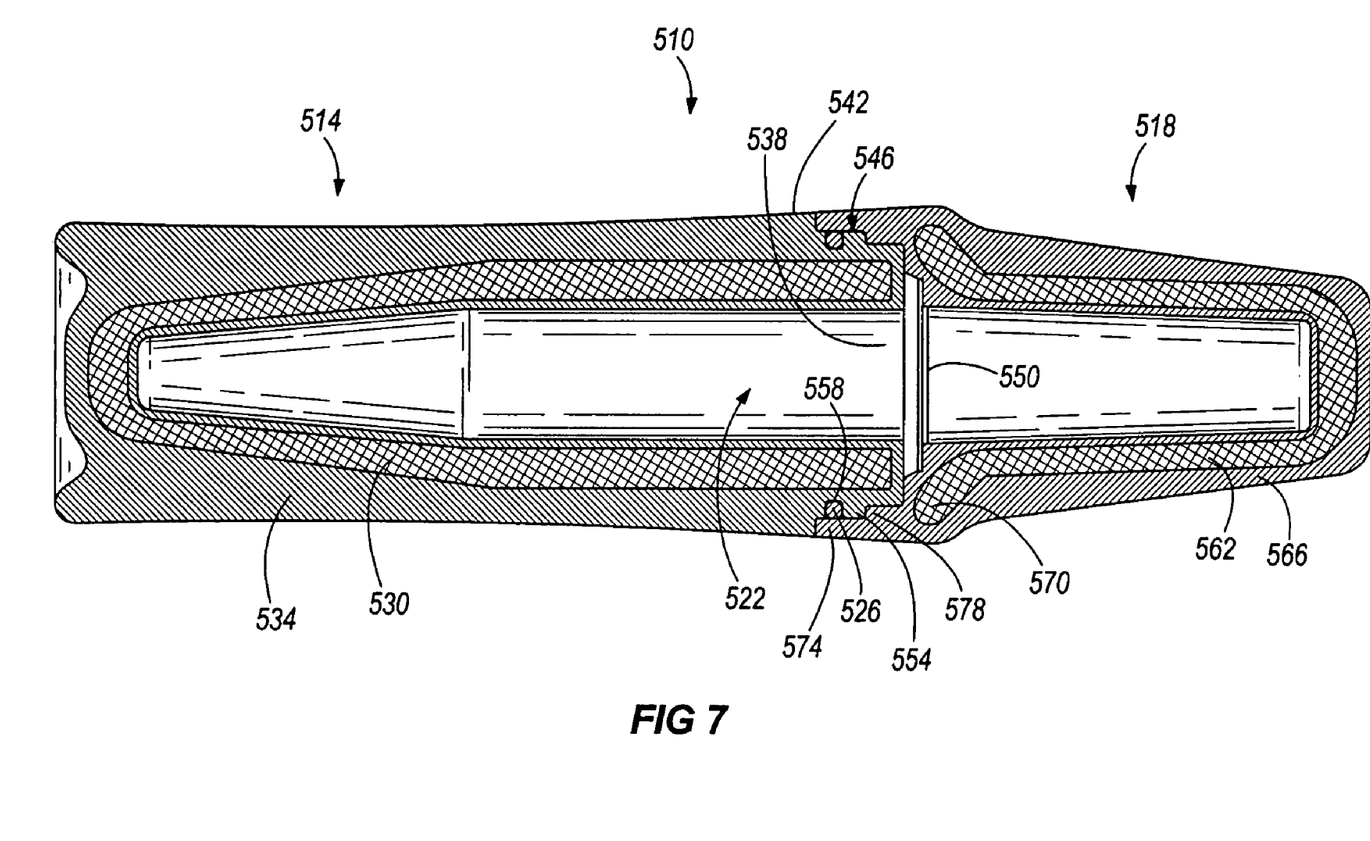
FIG. 7 is a sectional view of another embodiment of a radiation-shielding container.

FIG. 7 illustrates another embodiment of a radiation-shielding container. A container 510 includes a body assembly 514 and a cap assembly 518 removably securable to the body assembly 514. When secured, the body assembly 514 and the cap assembly 518 define a chamber 522 for storing a syringe (not shown). The container 510 also includes a resilient O-ring 526 that provides a fluid-tight seal between the body assembly 514 and the cap assembly 518 when the two are secured together.

The body assembly 514 includes a shield 530 formed of radiation shielding material (such as lead, tungsten or the like) and a protective coating 534, or shell, that surrounds and encases the shield 530. The shield 530 has a generally cylindrical shape and has a thickness sufficient to prevent or reduce exposure of radiation emitted by the radiopharmaceutical. In the illustrated embodiment, the thickness of the shield 530 is about 0.25 inches. The shield 530 is overmolded with a homogenous thermoplastic elastomer or thermoset, to form the protective coating 534. The protective coating 534 surrounds and encases the shield 530 to coat all exposed surfaces of the shield 530.

Proximate an open end 538 of the body assembly 514, a portion of an outer surface 542 of the protective coating 534 defines a cap-securing structure 546 that extends into an open end 550 of the cap assembly 518. The securing structure 546 defines a plurality of radially outwardly and circumferentially extending ribs 554. The cap-securing structure 546 defines a reduced diameter of the outer surface 542 relative to the remaining portion of the outer surface. Axially spaced from the ribs 554 and the open end 538 of the body assembly 514 is an annular groove 558 that adapted to receive the O-ring 526. The O-ring 526 engages the cap assembly 518 to substantially seal the chamber 522 when the cap assembly 518 is secured to the body assembly 514.

The cap assembly 518 includes a shield 562 formed of radiation shielding material (such as lead, tungsten or the like) and a protective coating 566, or shell, that surrounds and encases the shield 562. The shield 562 has a generally cylindrical shape and a first end of the shield 562 defines a flange portion 570. The shield 562 has a thickness sufficient to prevent or reduce exposure of radiation emitted by the radiopharmaceutical. In the illustrated embodiment, the thickness is about 0.15 inches. The shield 562 is overmolded with a homogenous thermoplastic elastomer or thermoset, to form the protective coating 566. The protective coating 566 surrounds and encases the shield 562 to coat all exposed surfaces of the shield 562.

Proximate the open end 550 of the cap assembly 518, the protective coating 566 includes a flange 574 that axially extends away from the first end of the shield 562. The flange 574 defines a body-securing structure in the form of radially inwardly extending projections 578. The projections 578 cooperate with the ribs 554 to provide a releasable attachment between the cap assembly 518 and the body assembly 514. To couple the cap assembly 518 to the body assembly 514, the cap-securing structure 546 is inserted into the open end 550 of the cap assembly 518 and the cap assembly 518, or the body assembly 514, is rotated approximately one-quarter turn to engage the ribs 554 with the projections 578. It should be readily apparent to those of skill in the art that in further embodiments other securing structure may be used to secure the body assembly 514 and the cap assembly 518, such as threaded portions, or the securing structure may be reversed between the two assemblies such that the externally projecting ribs are defined by the cap assembly 518 and the internally extending projections are defined by the body assembly 514. In a further embodiment, the body assembly and the cap assembly may include plugs to cover an open portion of the protective coatings, as described above with respect to FIG. 6.

Figure 8:
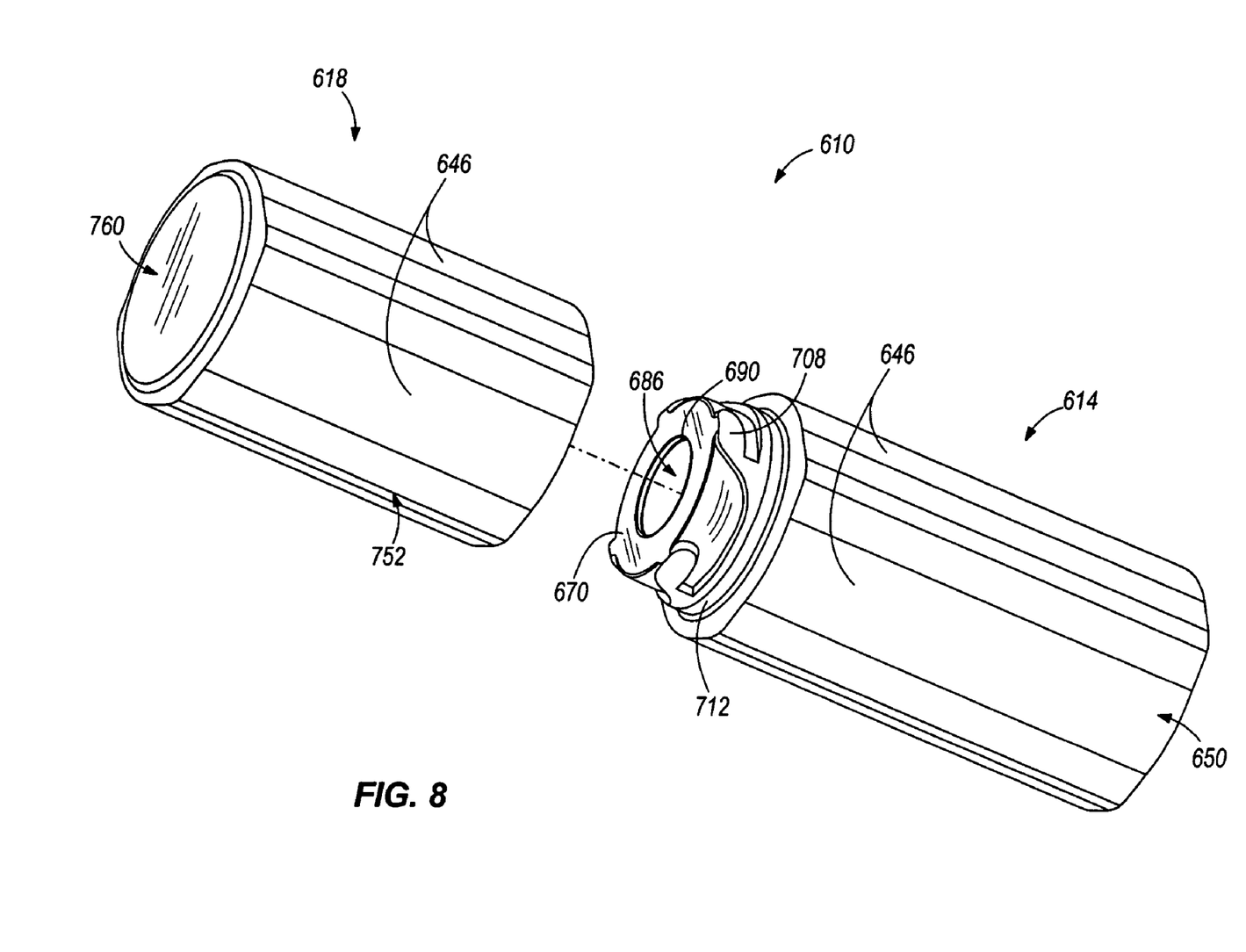
FIG. 8 is a perspective view of another embodiment of a radiation-shielding container embodying the invention.
Figure 9:
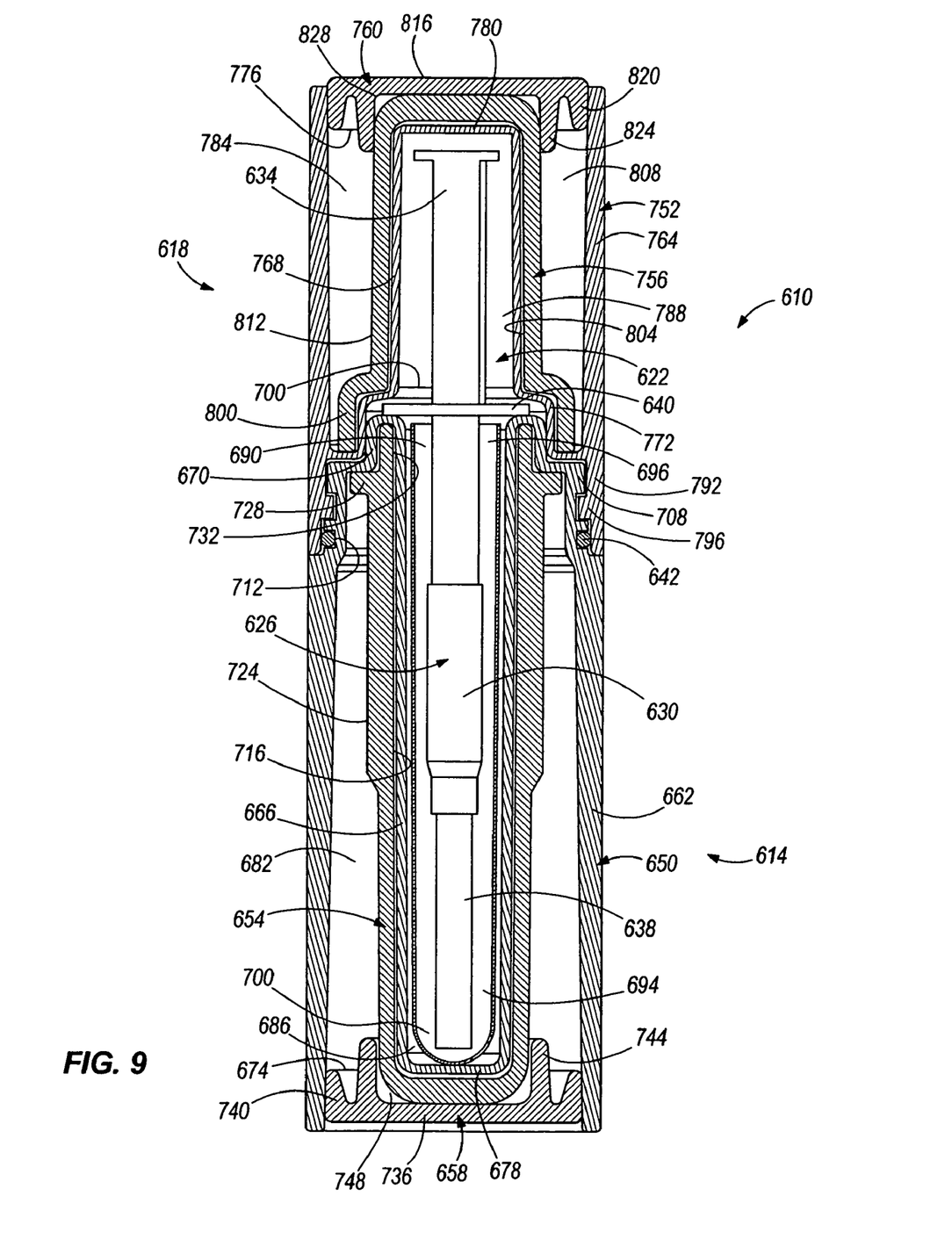
FIG. 9 is a sectional view of the radiation-shielding container shown in FIG. 8.

FIGS. 8 and 9 illustrate another embodiment of a radiation-shielding container. A container 610 includes a body assembly 614 and a cap assembly 618 removably securable to the body assembly 614. When secured, the body assembly 614 and the cap assembly 618 define a chamber 622 for storing a syringe 626. The syringe 626 includes a generally cylindrical body 630, a plunger 634 that depends from one end of the body 630, and a needle (not shown) that extends from an opposite end of the body 630 and is protected by an optional, removable cap 638. The body 630 defines a radially extending flange 640 at the plunger end that facilitates movement of the plunger 634 with respect to the body 630.

The container 610 includes a resilient O-ring 642 that provides a fluid-tight seal between the body assembly 614 and the cap assembly 618 when the two are secured together. In the illustrated embodiment, the body assembly 614 and the cap assembly 618 include a plurality of flats 646, such that each assembly 614, 618 preferably has a substantially rectangular shape, which provide grips to facilitate opening and closing of the container 610.

Referring to FIG. 9, the body assembly 614 includes a shell 650, a shield 654 formed of radiation shielding material that is received within the shell 650, and a plug 658 that retains the shield 654 within the shell 650. The shell 650 is generally cylindrical on the inside and includes an outer wall 662, an inner wall 666 spaced apart from the outer wall 662, a stepped first end wall 670 extending between the outer wall 662 and the inner wall 666, and an open end 674 opposite the end wall 670. A second end wall 678 extends between ends of the inner wall 666 opposite the first end wall 670 and adjacent the open end 674. The outer wall 662, the inner wall 666, and the end walls 670, 678 define a cavity 682 for receiving the shield 654. The inner wall 666 and the second end wall 678 define a first chamber portion 686 for housing at least the body 630 and the needle of the syringe 626, wherein the inner wall 666 and the second end wall 678 separate the cavity 682 and the first chamber portion 686. In FIG. 3, an opening 690 of the first chamber portion 686 is located at one end of the body assembly 614 and the open end 674 of the shell 650 is located at an opposite end of the body assembly 614.

In the illustrated embodiment, a removable liner 694, or bio-liner, is positioned within the first chamber portion 686 of the body assembly 614. The liner 694 has a generally cylindrical shape including an open end 696 and a closed end 700. The liner 694 extends substantially along the inner wall 666 of the shell 650, and is sized and configured to receive at least the body 630 and the needle of the syringe 626. The liner 694 prevents fluid contamination of the body assembly 614 if the protective cap 638 is removed from the syringe 626. In a further embodiment, the liner 694 may not be included in the body assembly 614, or the liner 694 may have other shapes. It should be readily apparent to those of skill in the art that other embodiments of a radiation-shielding container may include the bio-liner 694.

Proximate the opening 690 of the first chamber portion 686, a portion of the outer wall 662 of the shell 650 defines a cap-securing structure that extends into an opening 704 of the cap assembly 618. In the illustrated embodiment, the securing structure is positioned rearward of the first end wall 670. The securing structure defines a plurality of radially outwardly and circumferentially extending ribs 708. In the illustrated embodiment, four ribs 708 are provided and are substantially equally spaced about the circumference of the opening 690. Axially spaced from the ribs 708 and the first end wall 670 is an annular groove 712 that is adapted to receive the O-ring 642. The O-ring 642 engages the cap assembly 618 to substantially seal the chamber 622 when the cap assembly 618 is secured to the body assembly 614, as set forth hereafter. In the illustrated embodiment, the shell 650 is comprised of a suitable plastic, such as polycarbonate ABS blend, and is formed by injection molding.

The base assembly 614 includes the shield 654 formed of radiation shielding material, such as lead, tungsten, or the like. The shield 654 has a generally cylindrical shape and is received within the cavity 682 of the shell 650. An inner surface 716 of the shield 654 lies adjacent the inner wall 666 and the second end wall 678 of the shell 654, however, in the illustrated embodiment there is a clearance fit between the shield 654 and the shell 650. A gap 720 is formed between an outer surface 724 of the shield 654 and the outer wall 662 of the shell 650 such that the shield 654 does not fill the entire cavity 682. An outwardly extending radial flange 728 is axially spaced from an open end 732 of the radiation shield 54. The flange 728 and the open end 732 have a stepped configuration that complements the contour of and lies adjacent to the first end wall 670 of the body assembly 614.

The plug 658 covers the open end 674 of the shell 650 and retains the shield 654 within the shell 650. The plug 658 has a generally circular body portion 736 and an outer flange 740 extending axially inward from an outer circumference of the body portion 736, such that the plug 654 has a generally cylindrical shape. An inner flange 744 is spaced radially inward from the outer flange 740 and extends axially inward from the body portion 736. In use, the plug 658 is inserted into the open end 674 of the shell 650. In the illustrated embodiment, the inner flange 744 and a recess 748, which is defined by the body portion 736 and the inner flange 744, engages a closed end of the shield 654 and pushes the open end 732 of the shield 654 into contact with the first end wall 670 of the shell 650, while maintaining the clearance fit between the inner surface 716 of the shield 654 and the inner wall 666 and the second end wall 678. The plug 658 retains the shield 654 within the cavity 682 and mechanically holds the shield 654 in place within the cavity 682. In the illustrated embodiment, the outer flange 740 is secured to the outer wall 662 of the shell 650, such as by friction welding, bonding, a fastener, or the like. Further, the plug 658 is comprised of a suitable plastic, such as polycarbonate ABS blend, and is formed by injection molding.

Referring to FIG. 9, the cap assembly 618 includes a shell 752, a shield 756 formed of radiation shielding material that is received within the shell 752, and a plug 760 that retains the shield 756 within the shell 752. The shell 752 is generally cylindrical on the inside and includes an outer wall 764, an inner wall 768 spaced apart from the outer wall 764, a stepped first end wall 772 extending between the outer wall 764 and the inner wall 768, and an open end 776 opposite the end wall 772. A second end wall 780 extends between second ends of the inner wall 768 opposite the first end wall 772 and adjacent the open end 776.

The outer wall 764, the inner wall 768, and the end walls 772, 780 define a cavity 784 for receiving the shield 756. The inner wall 768 and the second end wall 780 define a second chamber portion 788 for housing at least the plunger 634 portion of the syringe 626, wherein the inner wall and the second end wall 780 separate the cavity 784 and the second chamber portion 788. The opening 704 of the second chamber portion 788 is located at one end of the cap assembly 618 and the open end 776 of the shell 752 is located at an opposite end of the cap assembly 618. In the illustrated embodiment, the shell 752 is comprised of a suitable plastic, such as polycarbonate ABS blend, and is formed by injection molding.

Proximate the first end of the cap assembly 618, an annular protrusion 792 axially extends from the outer wall 764 and the first end wall 772 of the shell 752. The annular protrusion 792 defines a body-securing structure in the form of radially inwardly extending projections 796. The projections cooperate with the ribs 708 of the cap-securing structure to provide a releasable attachment between the cap assembly 618 and the body assembly 614. To couple the cap assembly 618 to the body assembly 614, the cap-securing structure is inserted into the opening 704 of the second chamber portion 788 and the cap assembly 618, or the body assembly 614, is rotated approximately one-quarter turn to engage the ribs 708 with the projections 796. The flange portion 640 of the syringe 626 is caught between the first end wall 670 of the body assembly shell 650 and the first end wall 772 of the cap assembly shell 792, which holds the syringe 626 in place within the chamber 622.

In the illustrated embodiment, the body assembly 614 and the cap assembly 618 are secured together by a bayonet-type interlocking means. However, it should be readily apparent to those of skill in the art that in further embodiments other securing structure may be used to secure the body assembly 614 and the cap assembly 618, such as threaded portions, or the securing structure may be reversed between the two assemblies 614, 618 such that the externally projecting ribs on defined by the cap assembly 618 and the internally extending projections are defined by the body assembly 614.

The cap assembly 618 includes the shield 756 formed of radiation shielding material, such as lead, tungsten or the like. The shield 756 has a generally cylindrical shape and is received within the cavity 784 of the shell 752. A first end of the shield 756 defines an L-shaped flange portion 800 that complements the contour of and lies adjacent to the first end wall 772 of the shell 752. An inner surface 804 of the shield 756 lies adjacent the inner wall 768 and the second end wall 780 of the shell 752, however, in the illustrated embodiment there is a clearance fit between the shield 756 and the shell 752. A gap 808 is formed between an outer surface 812 of the shield 756 and the outer wall 764 of the shell 752 and the shield 756 does not fill the entire cavity 784. Referring to FIG. 9, the first end 800 of the shield 756 of the cap assembly 618 substantially surrounds the open end 732 of the shield 654 of the body assembly 614 such that the two shields overlap to prevent line of sight radiation leakage from the chamber 622.

The plug 760 covers the open end 776 of the shell 752 and retains the shield 756 within the shell 752. In the illustrated embodiment, the plug 760 of the cap assembly 618 is identical to the plug 658 of the body assembly 614 discussed above such that either plug could be used in the body assembly 614 or the cap assembly 618. The plug 760 has a generally circular body portion 816 and an outer flange 820 extending axially inward from an outer circumference of the body portion 816, such that the plug 760 has a generally cylindrical shape. An inner flange 824 is spaced radially inward from the outer flange 820 and extends axially inward from the body portion 816.

In use, the plug 760 is inserted into the open end 776 of the shell 752. In the illustrated embodiment, the inner flange 824 and a recess 828, which is defined by the body portion 816 and the inner flange 824, engages a closed end of the shield 756 and pushes opposite ends of the shield 756 into contact with the first end wall 772 of the shell 752, while maintaining the clearance fit between the inner surface 804 of the shield 756 and the inner wall 768 and the second end wall 780. The plug 760 retains the shield 756 within the cavity 784 and mechanically holds the shield 756 in place within the cavity. In the illustrated embodiment, the outer flange 820 is secured to an inner surface of the outer wall 764 of the shell 752, such as by friction welding, bonding, a fastener, or the like.

It should be readily apparent to those of skill in the art that other suitable materials and methods may be used for fabricating the radiation shields, shells, plugs, and protective coatings described above. For example, the shells and the plugs may be formed from ABS, polycarbonate, polyethylene, PVC, CPVC, acrylic, fiberglass, polypropylene, carbon fiber, UHMW polyethylene, Nylon, polystyrene, any form of plastic or fiber filled/woven epoxy, or the like. Further, the shells and plugs may be fabricated by other known methods, such as, but not limited to, machining and two-part epoxy based applications.

Various features and advantages of the invention are set forth in the following claims.

What is claimed is:

1. A radiation-shielding container for storing a syringe, the radiation-shielding container comprising:
 a body assembly for housing a portion of the syringe, the body assembly including a body shield formed of radiation shielding material, a body shell that defines a first cavity having an open end for receiving the body shield and defines a first chamber portion for receiving a portion of the syringe, wherein an inner wall of the body shell separates the first cavity and the first chamber portion, and a body plug secured to the body shell to cover the open end of the first cavity and retain the body shield within the first cavity; and
 a cap assembly for housing a portion of the syringe, the cap assembly including a cap shield formed of radiation shielding material, a cap shell that defines a second cavity having an open end for receiving the cap shield and defines a second chamber portion for receiving a portion of the syringe, wherein an inner wall of the cap shell separates the second cavity and the second chamber portion, and a cap plug secured to the cap shell to cover the open end of the second cavity and retain the cap shield within the second cavity, wherein the cap assembly is securable to the body assembly such that the first and second chamber portions define a chamber for storing the syringe.

2. The radiation-shielding container of claim 1 wherein the body shield is formed of lead.

3. The radiation-shielding container of claim 1 wherein the cap shield is formed of lead.

4. The radiation-shielding container of claim 1, and further comprising:
   a cap-securing structure including at least one radially outwardly and circumferentially extending rib defined by the shell of the body assembly; and
   a body-securing structure including at least one radially inwardly extending projection defined by the shell of the cap assembly for engagement with the cap-securing structure of the body assembly.

5. The radiation-shielding container of claim 1 wherein an inner surface of the body shield is positioned adjacent the inner wall of the body shell and extends substantially the length of the inner wall.

6. The radiation-shielding container of claim 5 wherein there is a clearance fit between the inner surface of the body shield and the inner wall of the body shell.

7. The radiation-shielding container of claim 1 wherein an inner surface of the cap shield is positioned adjacent the inner wall of the cap shell and extends substantially the length of the inner wall.

8. The radiation-shielding container of claim 7 wherein there is a clearance fit between the inner surface of the cap shield and the inner wall of the cap shell.

9. The radiation-shielding container of claim 1 wherein the body plug presses against the body shield to prevent movement of the body shield within the first cavity.

10. The radiation-shielding container of claim 1 wherein the cap plug presses against the cap shield to prevent movement of the cap shield within the second cavity.

11. The radiation-shielding container of claim 1, and further comprising a bio-liner received by the first chamber portion of the body assembly.

12. The radiation-shielding container of claim 1 wherein an open end of the cap shield substantially surrounds an open end of the body shield.

13. A radiation-shielding container for storing a syringe, the radiation-shielding container comprising:
   a body assembly for housing a portion of the syringe, the body assembly including
      a body shell having an outer wall, an inner wall spaced apart from the outer wall, an end wall connecting the outer wall to the inner wall, and an open end, wherein the inner wall defines a first chamber portion for receiving the syringe, and the outer wall, the inner wall and the end wall define a first cavity,
      a body shield formed of radiation shielding material and having a substantially cylindrical shape, the body shield disposed within the first cavity of the body shell wherein an inner surface of the body shield lies adjacent the inner wall of the body shell, and
      a body plug configured and adapted for receipt by the open end of the body outer shell to cover the open end, wherein the body plug retains the body shield within the first cavity; and
   a cap assembly for housing a portion of the syringe, wherein the cap assembly is securable to the body assembly, the cap assembly including
      a cap shell having an outer wall, an inner wall spaced apart from the outer wall, an end wall connecting the outer wall to the inner wall, and an open end, wherein the inner wall defines a second chamber portion for receiving the syringe, and the outer wall, the inner wall and the end wall define a second cavity,
      a cap shield formed of radiation shielding material and having a substantially cylindrical shape, the cap shield disposed within the second cavity of the cap shell wherein an inner surface of the cap shield lies adjacent the inner wall of the cap shell, and
      a cap plug configured and adapted for receipt by the open end of the cap shell to cover the open end, wherein the cap plug retains the shield within the second cavity.

14. The radiation-shielding container of claim 13 wherein the body shield is formed of lead.

15. The radiation-shielding container of claim 13 wherein the cap shield is formed of lead.

16. The radiation-shielding container of claim 13, and further comprising:
   a cap-securing structure including at least one radially outwardly and circumferentially extending rib defined by the shell of the body assembly; and
   a body-securing structure including at least one radially inwardly extending projection defined by the shell of the cap assembly for engagement with the cap-securing structure of the body assembly.

17. The radiation-shielding container of claim 13 wherein the outer wall of the body shell includes an annular groove, the radiation-shielding container further comprising a resilient O-ring positioned in the annular groove to provide a seal between the body and cap shells.

18. The radiation-shielding container of claim 13 wherein there is a clearance fit between the inner surface of the body shield and the inner wall of the body shell.

19. The radiation-shielding container of claim 13 wherein there is a clearance fit between the inner surface of the cap shield and the inner wall of the cap shell.

20. The radiation-shielding container of claim 13 wherein the body plug presses against the body shield to prevent movement of the body shield within the first cavity.

21. The radiation-shielding container of claim 13 wherein the cap plug presses against the cap shield to prevent movement of the cap shield within the second cavity.

22. The radiation-shielding container of claim 13 wherein the body plug is secured to the body shell.

23. The radiation-shielding container of claim 13 wherein the cap plug is secured to the cap shell.

24. The radiation-shielding container of claim 13, and further comprising a bio-liner received by the first chamber portion of the body shell.

25. The radiation-shielding container of claim 13 wherein an open end of the cap shield substantially surrounds an open end of the body shield.

26. A radiation-shielding container for storing a syringe, the radiation-shielding container comprising:
   a first assembly for housing a portion of the syringe, the first assembly including a shield formed of radiation shielding material, a shell that defines a first cavity having an open end for receiving the shield and defines a first chamber portion for receiving a portion of the syringe, wherein an inner wall of the shell separates the first cavity and the first chamber portion, and a plug secured to the shell to cover the open end of the first cavity and retain the shield within the first cavity; and a second assembly for housing a portion of the syringe, the second assembly including a shield formed of radiation shielding material and defining a second chamber portion, wherein the first and second assemblies are securable together such that the first and second chamber portions define a chamber for storing the syringe.

27. The radiation-shielding container of claim 26 wherein the second assembly comprises:

a shell that defines a cavity having an open end for receiving the shield of the second assembly and defines the second chamber portion for receiving a portion of the syringe, wherein an inner wall of the shell separates the cavity and the second chamber portion; and a plug secured to the shell to cover the open end of the cavity and retain the shield within the cavity.

28. The radiation-shielding container of claim 26 wherein the second assembly includes a protective coating that substantially surrounds and encases the shield.

29. The radiation-shielding container of claim 28 wherein an open portion is formed in the protective coating, the second assembly including a plug fitted within the open portion to cover the shield.

30. A method of forming a radiation-shielding container for a syringe, the radiation-shielding container including a first shell and a second shell, each shell having an outer wall, an inner wall spaced apart from the outer wall, an end wall connecting the outer wall to the inner wall, and an open end, wherein the inner wall defines a chamber portion, and the outer wall, the inner wall and the end wall define a cavity, the method comprising:

placing a first shield in the cavity of the first shell, the first shield formed of radiation shielding material, wherein an inner surface of the first shield is positioned adjacent the inner wall of the first shell;

covering the open end of the first shell to retain the first shield within the cavity of the first shell;

placing a second shield in the cavity of the second shell, the second shield formed of radiation shielding material, wherein an inner surface of the second shield is positioned adjacent the inner wall of the second shell;

covering the open end of the second shell to retain the second shield within the cavity of the second shell;

placing a syringe within the chamber portion of the first shell; and securing the second shell to the first shell wherein the syringe is confined within the chamber portions of the first and second shells.

31. The method of claim 30 wherein covering the open end of the first shell comprises securing a plug to the outer wall of the first shell.

32. The method of claim 31 wherein the plug prevents movement of the first shield within the first shell.

33. The method of claim 30 wherein covering the open end of the second shell comprises securing a plug to the outer wall of the second shell.

34. The method of claim 33 wherein the plug prevents movement of the second shield within the second shell.

* * * * *